United States Patent [19]

Bonaldi et al.

[11] Patent Number: 5,362,891
[45] Date of Patent: Nov. 8, 1994

[54] PROCESS FOR THE PREPARATION OF TAURINE-CONJUGATED BILE ACIDS

[75] Inventors: Antonio Bonaldi, Chiuduno; Egidio Molinari, Longone al Segrino, both of Italy

[73] Assignee: Erregierre Industria Chimica S.p.A., S. Paolo D'Argon, Italy

[21] Appl. No.: 97,103

[22] Filed: Jul. 26, 1993

[30] Foreign Application Priority Data

Aug. 4, 1992 [IT]  Italy .......................... MI92 A 001925

[51] Int. Cl.$^5$ .............................................. C07J 1/00
[52] U.S. Cl. ...................................................... 552/554
[58] Field of Search ........................................ 552/554

[56] References Cited

U.S. PATENT DOCUMENTS 3,580,936  5/1971  Patchett et al. ............... 552/554
4,565,810  1/1986  Castagnola ..................... 552/554

Primary Examiner—Johann Richter
Assistant Examiner—Rebecca Cook
Attorney, Agent, or Firm—Hedman, Gibson & Costigan

[57] ABSTRACT

Process for the preparation of taurine-conjugated biliary acids of general formula (I):

$$(Y-NH-CH_2-CH_2-SO_3)_l M \qquad (I)$$

where Y is the acyl of a biliary acid selected from the group consisting of ursodeoxycholic, chenodeoxycholic, lithocholic, $3\alpha$-$7\beta$-$12\alpha$-tri-hydroxycholanic, $3\alpha$-$7\beta$-dihydroxy-12-ketocholanic, deoxycholic, dehydrocholic, iodeoxycholic, iocholic acids; M is H, Na, K, Mg, Ca; l is 1 or 2, being 2 when M=Mg or Ca.

10 Claims, No Drawings

PROCESS FOR THE PREPARATION OF TAURINE-CONJUGATED BILE ACIDS

FIELD OF THE INVENTION

The present invention relates to a process for the preparation of taurine-conjugated biliary acids or pharmaceutically acceptable salts thereof.

STATE OF THE ART

The amides of biliary acids linked to the amino acids, glycine and taurine, are known as conjugated biliary acids and relevant biliary salts.

The biliary acids secreted by the liver are almost entirely in the conjugated form. For example, glycoursodeoxycholic acid is the main metabolite accumulating in biliary after ursodeoxycholic acid prolonged administration.

The synthesis of biliary acids conjugated with taurine and glycine was described by Bergström and Norman (Enciclopedia della Chimica, USES, Firenze, pages 421-426).

According to said process, a mixed anhydride was obtained by treating biliary acid salt and tributylamine with ethylchlorocarbonate in dioxane at low temperature. The obtained anhydride was reacted with a glycine or taurine sodium salt aqueous solution to produce the sodium salt of the conjugated acid, However, the product yields and, especially, purity obtained by the aforesaid process are not high.

THE PRESENT INVENTION

It has surprisingly been found that taurine-conjugated biliary acids or their pharmaceutically acceptable salts, of general formula (I):

$$(Y-NH-CH_2-CH_2SO_3)_nM \qquad (I)$$

where Y is the acyl of a biliary acid selected from the group consisting of ursodeoxycholic, chenodeoxycholic, lithocholic, $3\alpha$-$7\beta$-$12\alpha$-tri-hydroxycholanic, $3\alpha$-$7\beta$-dihydroxy-12-ketochoianic, deoxycholic, dehydrocholic, iodeoxycholic, iocholic acids: M is H. Na, K, ME, Ca; n is 1 or 2, and is 2 when M=Mg or Ca, can be prepared according to a process not adversely affected by the disadvantages inherent in the known process.

Like the process known from literature, the process of this invention consists of:

a) salifying the biliary acid of formula (II)

$$Y-OH \qquad (II)$$

where Y is as defined above, with a tertiary amine of alkyl or heteroaromatic type in an aprotic solvent at a temperature below 20° C.;

b) reacting either the mixture obtained in (a) containing the aforesaid biliary acid salt or previously isolated salt, with a chloroformate of general formula (III):

$$Cl-COOR \qquad (III)$$

where R is selected from the group consisting of $C_1$-$C_5$ alkyl, phenyl, benzyl, at a temperature below 20° C. in the presence of an aprotic solvent to give the corresponding mixed anhydride of formula (IV)

$$Y-O-COOR \qquad (IV)$$

where Y and R are as defined above.

But, unlike the process known from literature, the process of the present invention is characterized by the following steps:

c) mixed anhydride (IV) is reacted with a phenol of general formula (V):

where R1 is selected from H, $C_1$-$C_5$ alkyl, $C_2$-$C_5$ acyl and nitro group, at a temperature below 60° C. in the presence of an aprotic solvent and of a tertiary amine used in step (a) to give the corresponding phenol ester of formula (VI):

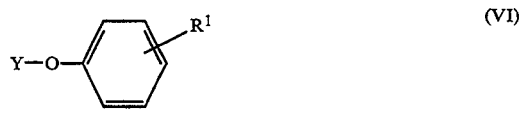

where Y and R1 are as defined above;

d) the product is separated by water addition, extraction of phenol ester in a solvent, evaporation and crystallization, optionally followed by recrystallization;

e) phenol ester is treated with an aqueous solution of taurine as such or in the form of an alkaline metal salt or of a tertiary amine of alkyl or heteroaromatic type, at a temperature ranging from 0° C. to 100° C. (ammonlysis) optionally in the presence of a protic solvent;

f) the reaction mixture is extracted with ethyl acetate and the obtained aqueous phase is acidified to a pH between 0 and 1, in order to precipitate the desired product, which is filtered:

g) the product collected in (f) is crystallized in a protic or aprotic polar solvent.

The process of the present invention—which envisages the essential steps of producing an intermediate, i.e. phenol ester (VI), and removing same from the reaction mixture by crystallization—gives high yields of product with high degree of purity.

DETAILED DESCRIPTION OF THE INVENTION

The solvent used in steps (a) and (b) of the process of the present invention may be either an aprotic polar solvent, preferably acetone, ethyl acetate, dioxane, tetrahydrofuran, or an aprotic dipolar solvent, e.g. dimethylformamide.

The intermediates obtained in steps (a) and (b) may be either isolated or not: in the latter case the solvent used in step (a) of the process according to the invention is the same as that used in step (b).

The tertiary amines used in steps (a) and (c) to give the biliary acid salt and phenol salt, respectively, are preferably selected from triethylamine, tributylamine, and pyridine.

The $C_1$-$C_5$ alkyl chloroformate (III) used in (b) is preferably methyl or ethyl chloroformate.

The aprotic solvent used in (c) may be an aprotic polar solvent selected from acetone, ethyl acetate, dioxane, tetrahydrofuran, or an aprotic dipolar solvent, i.e. N,N-dimethylformamide.

The solvent used to crystallize phenol ester (VI), step (d) of the process of the present invention, is a polar solvent, either protic or aprotic, such as, e.g., $C_1$-$C_4$ alcohol, or an aprotic polar solvent, e.g. acetone and acetic acid esters with $C_1$ to $C_4$ alcohols, preferably acetonitrile either alone or mixed with the aforesaid alcohols.

The bases used to obtain the taurine salt used in step (e) of the process of the present invention are selected from: sodium hydroxide, potassium hydroxide, lithium hydroxide, potassium and sodium carbonate or bicarbonate, as well as the tertiary alkyl amines preferably used in step (a) for biliary acid salt production. The solvent used in the aforementioned ammonolysis—step (e) of the process of the present invention—is a polar solvent, such as water either alone or mixed with $C_1$ to $C_4$ alcohol.

The acid used in step (f) for conjugated raw acid (I) precipitation is a mineral acid, such as hydrochloric, or hydrobromic acid, or an organic acid such as methanesulphonic acid.

The solvent used in step (g) of the process of the present invention for conjugated biliary acid (I) crystallization is a protic polar solvent, such as e.g. water or an alcohol, and preferably ethanol, isopropanol, sec-butanol, or an aprotic polar solvent, such as acetone, or $C_1$-$C_4$ alcohol acetates and preferably ethyl acetate.

The following examples are illustrative only; in no event are they to be regarded as limiting the scope of the invention.

EXAMPLE 1

Ursodeoxycholic acid (250 g) was suspended in dioxane (1000 ml) and treated with triethylamine (66 g). The mixture was stirred at room temperature for 1 hr. After cooling to 10° C., ethyl chloroformane (70 g) was added dropwise at a temperature maintained below 20° C. After addition, the mixture was stirred at 15° C.-20° C. for 1 hr, poured into a solution prepared separately by dissolving p-hydroxypropiophenone (150 g) in ethyl acetate (500 ml) and triethylamine (101 g) and by heating the obtained solution to 35° C.-40° C., which temperature was maintained during the dropwise addition and for one or two more hours.

Addition of deionized water (1000 ml) gave two phases. The organic phase was washed with deionized water (500 ml) and evaporated to a thick oil, which was crystallized with acetonitrile (1500 ml) by heating and subsequent cooling to 15° C.

The precipitate was separated by filtration and washed thoroughly with acetonitrile.

Drying yielded 300 g of ursodeoxycholic acid ester having the following characteristics:

crystalline white powder m.p.=88°-92° C. $[\alpha]_D^{20}=+41.5°$ C.

Ammonolysis: taurine (105 g) was dissolved in deionized water (525 ml) and sodium hydroxide pearls (33.5 g). The solution was added with sec-butyl alcohol (300 ml) and phenol ester (300 g) obtained as described above.

The solution was refluxed for 5 hrs. Ethyl acetate (1000 g) was added and phases were allowed to separate. The alkaline aqueous phase, after the remaining solvent is distilled, was added with deionized water (300 ml). Tauroursodeoxycholic acid was precipitated by acidification with 37% hydrochloric acid (200 g).

The product was filtered by washing with 2×50 ml deionized water. The obtained raw product was purified by recrystallization after hot dissolution with distilled water (700 ml), followed by cooling to 0° C., filtering and washing with distilled water. After drying 220 g of tauroursodeoxycholic acid with the following characteristics was obtained:

crystalline white powder m.p.=144°-145° C. $[\alpha]_D^{20}=+46°$ C. (C=2% in ethanol) Water residue=6.9% Titre obtained by titrating with 0.1N NaOH=93.2% corresponding to 100.1% on dry basis.

EXAMPLE 2

Phenol ester was obtained following the same procedure of Example 1, but using ethyl acetate instead of dioxane as reaction solvent for mixed anhydride preparation. 310 grams phenol ester with the following characteristics was obtained:

m.p.=89°-92° C. $[\alpha]_D^{20}=+42.1°$

Ammonolysis was carried out according to the same procedure of Example 1, but using, n-butyl alcohol instead of sec-butyl alcohol, and 130 g of 48% hydrobromic acid instead of hydrochloric acid in tauroursodeoxycholix precipitation.

215 grams tauroursodeoxycholic acid with the following characteristics was obtained:

crystalline white powder m.p.=145°-147° C. $[\alpha]_D^{20}=+45.7°$ (C=2% in ethanol) Water residue=7% Titre obtained by titration with (0.1N NaOH)=92.8% corresponding 99.8% on dry basis.

EXAMPLE 3

Iodeoxycholic acid (250 g) was suspended in ethyl acetate (1500 ml) and treated with triethylamine (66 g). The mixture was stirred at 50° C. for ½ hr. After cooling to 5° C., ethyl chloroformate (70 g) was added dropwise at a temperature maintained below 15° C. After addition, the mixture was stirred at 15° C.-20° C. for ½ hr. poured into a solution prepared separately by dissolving p-hydroxypropiophenone (150 g) in ethyl acetate (500 ml) and triethylamine (50.5 g) and by heating the obtained solution to 20° C.-25° C., which temperature was maintained during the dropwise addition and for one or two more hours.

Addition of deionized water (1000 ml) gave two phases. The organic phase was washed with deionized water (500 ml) and evaporated to a thick oil, which was crystallized with acetonitrile (1500 ml) by heating and subsequent cooling.

The precipitate was separated by filtration and washed thoroughly with acetonitrile.

Drying yielded 280 g phenol ester having the following characteristics:

m.p.=148°-150° C. $[\alpha]_D^{20}=+3.83°$ (C=2% in ethanol)

Ammonolysis: taurine (98 g) was dissolved in deionized water (500 ml) and sodium hydroxide pearls (1.15 g). The solution was added with sec-butyl alcohol (280 ml) and iodeoxycholic acid phenol ester (280 g) obtained as described above.

The solution was refluxed for 5 hrs. Ethyl acetate (1000 g) was added and phases were allowed to separate. The alkaline aqueous phase, after the remaining solvent is distilled, was added with deionized water (300 ml). Tauroiodeoxycholic acid was precipitated by acidification with 48% hydrobromic acid (150 g).

The raw product was filtered by washing with 2×100 ml deionized water.

The obtained raw product was dried and purified by boiling with acetone (700 ml). After cooling to 10° C., the product was filtered and washed with acetone (100 ml). After drying, 200 g of tauroiodeoxycholic acid with the following characteristics was obtained:

crystalline white powder m.p.=168°−169° C. [α]$_D^{20}$=+6.08° (C=2% in ethanol) Loss on drying=2% Titre=97.92% corresponding to 99.92% on dry basis.

We claim:

1. A process for the preparation of a taurine-conjugated biliary acid or salt thereof of general formula (I):

(Y—NH—CH$_2$—CH$_2$—SO$_3$)$_n$M   (I)

where Y is the acyl of a biliary acid selected from the group consisting of ursodeoxycholic, chenodeoxycholic, lithocholic, 3α-7β-12α-tri-hydroxycholanic, 3α-7β-dihydroxy-12-ketocholanic, deoxycholic, dehydrocholic, iodeoxycholic and iocholic acids; M is selected from the group consisting of H, Na, K, Mg and Ca; and n is 1 or 2, being 2 when M=Mg or Ca comprising the steps of:

a) salifying a biliary acid of formula (II)

Y—OH   (II)

where Y is as defined above, with an alkyl or heteroaromatic tertiary amine in an aprotic polar solvent at a temperature below 20° C. and optionally isolating said salified biliary acid;

b) treating either the reaction mixture containing the aforesaid biliary acid salt or previously isolated salt, with a chloroformate of general formula (III):

Cl—COOR   (III)

where R is selected from the group consisting of C$_1$-C$_5$alkyl, phenyl and benzyl, at a temperature below 20° C. in the presence of an aprotic polar solvent to give the corresponding mixed anhydride of formula (IV)

Y—O—COOR   (IV)

where Y and R are as defined above and optionally isolating said mixed anhydride;

c) reacting mixed anhydride (IV) with a phenol of general formula (V):

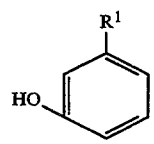   (V)

where R$^1$ is selected from the group consisting of H, C$_1$-C$_5$ alkyl, C$_2$-C$_5$ acyl and nitro group at a temperature below 60° C. in the presence of an aprotic solvent and of a tertiary amine to give the corresponding phenol ester of formula (VI):

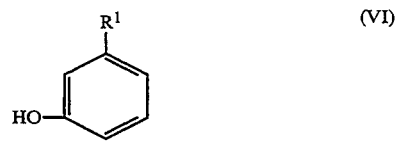   (VI)

d) separating the intermediate (VI) by water addition, phenol ester extraction in a protic or aprotic polar solvent, evaporation and crystallization, optionally followed by recrystallization;

e) treating the phenol ester coming from step (d) with an aqueous solution of taurine as such or in the form of a salt of an alkaline metal or of an alkyl or heteroaromatic tertiary amine at a temperature ranging from 0° C. to 100° C. optionally in the presence of a protic solvent;

f) extracting the reaction mixture with ethyl acetate and acidifying the obtained aqueous solution to a pH between 0 and 1 with a mineral acid or an organic acid for the precipitation of the desired product, which is filtered;

g) crystallizing the product collected in (f) in a polar solvent which is protic or aprotic.

2. The process according to claim 1 wherein the aprotic solvent used in steps (a) and (b) is an aprotic polar solvent selected from the group consisting of acetone, ethyl acetate, dioxane, and tetrahydrofuran or in aprotic depolar solvent which is dimethylformamide.

3. The process according to claim 1 wherein the intermediates obtained in (a) and (b) are not isolated.

4. The process according to claim 1 wherein the tertiary amines used in (a) and (c) to give the biliary acid salt and phenol salt, respectively, are selected from the group consisting of triethylamine, tributylamine, and pyridine.

5. The process according to claim 1 wherein C$_1$-C$_5$ alkyl chloroformate (III) used in (b) is a methyl or an ethylchloroformate.

6. The process according to claim 1 wherein the aprotic solvent used in (c) is an aprotic polar solvent selected from the group consisting of acetone, ethyl acetate, dioxane and tetrahydrofuran or an aprotic dipolar solvent.

7. The process according to claim 1 wherein the phenol ester crystallization solvent in step d is a protic solvent.

8. The process according to claim 1 wherein the base used to obtain the taurine salt used in step (e) are selected from the group consisting of sodium hydroxide, potassium hydroxide, lithium hydroxide, potassium carbonate, potassium bicarbonate, sodium carbonate, sodium bicarbonate, triethyl amine, tributyl amine and pyridine.

9. The process according to claim 1 wherein the acid used in step (f) for conjugated raw acid (I) precipitation is an acid selected from the group consisting of hydrochloric acid, hydrobromic acid and methanesulphonic acid.

10. The process according to claim 1 wherein the solvent used for conjugated biliary acid (I) crystallization in step g is a protic polar solvent consisting of water or an alcohol or an aprotic polar solvent consisting of acetone or C$_1$-C$_4$ alcohol acetate.

* * * * *